US006235797B1

(12) United States Patent
Elliot et al.

(10) Patent No.: US 6,235,797 B1
(45) Date of Patent: May 22, 2001

(54) RUTHENIUM ON RUTILE CATALYST, CATALYTIC SYSTEM, AND METHOD FOR AQUEOUS PHASE HYDROGENATIONS

(75) Inventors: Douglas C. Elliot, Richland; Todd A. Werpy, West Richland; Yong Wang; John G. Frye, Jr., both of Richland, all of WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 09/389,389

(22) Filed: Sep. 3, 1999

(51) Int. Cl.$^7$ .................................................. C07C 27/00
(52) U.S. Cl. ............................................. 518/715; 568/863
(58) Field of Search ............................. 518/715; 568/863

(56) References Cited

U.S. PATENT DOCUMENTS

| 2,868,847 | 1/1959 | Boyers ................................ 260/635 |
| 4,042,614 | 8/1977 | Vannice et al. .................... 260/449 R |
| 4,380,679 | 4/1983 | Arena ................................. 568/863 |
| 4,380,680 | 4/1983 | Arena ................................. 568/863 |
| 4,413,152 | 11/1983 | Arena ................................. 568/863 |
| 4,487,980 | 12/1984 | Arena ................................. 568/863 |
| 4,496,780 | 1/1985 | Arena ................................. 568/861 |
| 4,503,274 | 3/1985 | Arena ................................. 568/863 |
| 4,510,339 | 4/1985 | Arena ................................. 568/863 |
| 4,567,205 | 1/1986 | Arcuri et al. ....................... 518/715 |
| 5,616,154 | 4/1997 | Elliot et al. ........................ 48/197 R |
| 5,814,112 | 9/1998 | Elliot et al. ........................ 48/197 R |

FOREIGN PATENT DOCUMENTS

| 0 741 107 | 11/1996 | (EP) ............................................ 3/38 |
| 0 936 184 | 8/1999 | (EP) ............................................ 7/4 |

OTHER PUBLICATIONS

"Low Temperature Catalytic Gasification Of Wet Industrial Wastes," FY 1991–1992 Interim Report, Elliot et al., pp. B–16, B–17 Jun. 1993.

"Low Temperature Catalytic Gasification Of Wet Industrial Wastes," FY 1991–1992 Interim Report, Elliott et al., pp. 23, 25, Mar. 1995.

Degussa–Hüls Product Literature, "Fixed Bed Catalysts".

Primary Examiner—Elli Peselev
(74) Attorney, Agent, or Firm—Stephen R. May

(57) ABSTRACT

An essentially nickel- and rhenium-free catalyst is described comprising ruthenium on a titania support where the titania is greater than 75% rutile. A catalytic system containing a nickel-free catalyst comprising ruthenium on a titania support where the titania is greater than 75% rutile, and a method using this catalyst in the hydrogenation of an organic compound in the aqueous phase is also described.

24 Claims, No Drawings

RUTHENIUM ON RUTILE CATALYST, CATALYTIC SYSTEM, AND METHOD FOR AQUEOUS PHASE HYDROGENATIONS

This invention was made with Government support under Contract DE-AC0676RLO 1830 awarded by the U.S. Department of Energy. The Government has certain rights in the invention.

FIELD OF THE INVENTION

The present invention relates to catalysts having ruthenium disposed on a rutile support, catalytic systems containing such catalysts and at least one organic compound in water, and methods that use these catalysts in the hydrogenation of organic compounds in the aqueous phase.

BACKGROUND OF THE INVENTION

Hydrogenation reactions typically involve the reaction of hydrogen gas with an organic compound to produce a hydrogenated organic compound. Hydrogenation reactions are important in a variety of chemical processes including the production of fuels and the conversion of sugars to the corresponding polyalcohols. Despite generally favorable thermodynamics, there is a large kinetic barrier that slows the reaction of hydrogen gas with many unsaturated and heteronuclear organic compounds. To speed the reactions, it is necessary to add a catalyst, such as a metal. The metals that catalyze hydrogenations are usually expensive, and therefore it is common practice to increase the reactive surface area by distributing the metals over the surface of a support, thus forming a supported metal catalyst.

In addition to a supported metal catalyst, many commercial hydrogenations also require the use of organic solvents that dissolve the organic compounds and promote contact with the solid catalyst. Organic solvents, however, are often toxic and can present problems in storage, transportation, and disposal. Thus it would be desirable to avoid the use of organic solvents in hydrogenation reactions.

Instead of organic solvents, it would be desirable to use water to dissolve the organic compounds and promote contact with a solid catalyst. Furthermore, some organic compounds, such as sugars, are more soluble in water than in organic solvents. Thus, in many cases it would be advantageous to conduct hydrogenations in the presence of water, i.e., in the aqueous phase. On the other hand, many existing catalysts are not appropriate for aqueous phase reactions because they do not provide optimal conversion efficiency and yield. Moreover, in applications outside the laboratory, catalysts should remain active after weeks or months of processing; however, in aqueous phase processing conditions, the catalytic activity of existing catalysts becomes degraded or destroyed.

Some catalysts designed for aqueous phase hydrogenation reactions have been disclosed in prior patents. For example, Boyers in U.S. Pat. No. 2,868,847 discloses examples in which hydrogenations were carried out over catalysts of ruthenium on carbon or ruthenium on alumina. Arena, in U.S. Pat. Nos. 4,380,679, 3,380,680, 4,413,152, and 4,503,274, discloses aqueous phase hydrogenations of various carbohydrates over a catalyst supported on carbonaceous pyropolymer, alpha-alumina, titanated alumina, and gamma-alumina, respectively. In U.S. Pat. No. 4,487,980, Arena discloses aqueous phase hydrogenations and an aqueous phase hydrogenation catalyst comprising ruthenium and a titania-containing support. Arena analyzed leaching from a titania-bentonite material and studied the aqueous phase hydrogenation of glucose to sorbitol. Arena did not disclose the stability of the catalyst and did not disclose a rutile-containing catalyst.

Ruthenium on titania catalysts have long been known for catalyzing non-aqueous phase reactions. For example, Arcuri et al., in U.S. Pat. No. 4,567,205, disclose a ruthenium on titania catalyst for use in Fischer-Tropsch catalysis in which carbon monoxide and hydrogen gas are reacted to produce hydrocarbons. Arcuri et al. used rhenium in the catalyst to improve activity maintenance in Fischer-Tropsch conditions. Arcuri et al. state that the rhenium:ruthenium weight ratio ranges from about 10:1 to about 1:10. Arcuri et al. also state that the titania support is preferred to have a rutile:anatase ratio of at least 2:3 and found that under Fischer-Tropsch conditions, a rutile:anatase ratio of 2:1 demonstrated superior activity maintenance as compared to ratios of 1.2:1 and 30:1.

Ongoing research at Battelle Pacific Northwest Division has produced numerous discoveries in the area of low temperature catalytic gasification of wet industrial wastes. Elliott et al. have tested various types of supports in high pressure, hot water and found that supports such as γ- and δ-alumina and alumina-borate were unstable, but various other commercial supports such as titania and zirconia were reported to be relatively stable—see Low Temperature Catalytic Gasification of Wet Industrial Wastes, FY 1991–1992 and FY 1993–1994, pages B 16–17 and 23, 25, respectively. Elliott et al., in U.S. Pat. No. 5,814,112, disclose a nickel/ruthenium catalyst on a porous support for aqueous phase reactions. It is suggested that the porous support could be alumina, titania in the rutile form, zirconia in the monoclinic form, granulated carbon, böhmite, or a commercial G1-80 catalyst.

Despite considerable efforts, there remains a need for aqueous phase hydrogenation catalysts that maintain catalytic activity for extended periods of time under hydrogenation conditions. There also exist needs for aqueous phase hydrogenation catalysts that exhibit excellent conversion efficiencies, high selectivities, operability at low temperatures, and/or high processing rates.

SUMMARY OF THE INVENTION

The present invention provides a catalyst that has an active metal on a titania support. The active metal includes ruthenium and the titania is more than 75% rutile as measured by x-ray diffraction. Additionally, the catalyst is essentially nickel- and rhenium-free.

In a second aspect, the invention provides a catalytic system that includes a catalyst, at least one organic compound, and water. The catalyst is essentially nickel-free and includes ruthenium on a titania support, where the titania is more than 75% rutile as measured by x-ray diffraction.

In another aspect, the invention provides a method of hydrogenating an organic compound in the aqueous phase in which a feedstock contacts hydrogen in a catalytic system. The feedstock comprises at least one organic compound in water.

It is an object of the invention to provide a hydrogenation catalyst that is stable under aqueous phase operating conditions. It is another object of the invention to provide for the hydrogenation of organic compounds. Another object of the invention is to produce a hydrogenated product stream with extremely low levels of dissolved metal atoms. It is a further object to provide a catalyst that is essentially without nickel. It is yet another object of the invention to provide a catalyst that is essentially without rhenium. Other objects of the invention include the provision of hydrogenation reactions that possess excellent conversion efficiencies, high yields, operability at low temperatures, and/or high processing rates.

Although titania can occur in amorphous, brookite, anatase and rutile crystal structures, we have discovered that rutile is superior to the other forms as a support for ruthenium-catalyzed hydrogenations. The ruthenium on rutile catalyst provides numerous advantages that could not have been predicted prior to the present invention. These advantages include: enhanced stability as demonstrated by maintenance of catalytic activity after extended operating times; high conversion percentages at high processing rates and/or low temperatures; and high yields of desired hydrogenated products. Moreover, these desirable properties can be achieved without the use of modifying metals such as nickel or rhenium.

The subject matter of the present invention is particularly pointed out and distinctly claimed in the concluding portion of this specification. However, both the organization and method of operation, together with further advantages and objects thereof, may best be understood by reference to the following description.

DESCRIPTION OF THE PREFERRED EMBODIMENTS

The present invention provides a catalyst that has an active metal on a titania support. The active metal includes ruthenium and the titania is more than 75% rutile as measured by x-ray diffraction. Additionally, the catalyst is essentially nickel-free and, preferably, rhenium-free.

The active metal in the catalyst is ruthenium-based. In the catalysts of the present invention, ruthenium has been found have excellent catalytic activity and stability. Because ruthenium is expensive, it is desirable that ruthenium metal be distributed over the surface of a support in a manner that maximizes surface area of the ruthenium. The ruthenium preferably constitutes 0.1 to 10 weight % of the catalyst. Amounts of ruthenium above this range may not increase the catalyst's activity, while amounts below this range can have undesirably low processing rates. More preferably, ruthenium constitutes 1 to 5 weight % of the catalyst, and still more preferably 2 to 3 weight %.

Ruthenium is an especially stable and insoluble metal. The presence of other metals, however, may present problems such as toxic leachates or impaired catalytic activity. Thus, in a preferred embodiment, the active metal consists essentially of pure ruthenium. The ruthenium preferably constitutes at least 95 weight percent of the active metal, more preferably more than 98%, and still more preferably more than 99.8%.

The catalyst is essentially without nickel, that is, nickel does not make a significant contribution to the catalytic activity of the catalyst. Nickel is prone to dissolution in the aqueous phase processing conditions and may contaminate the product. This is especially a problem where a food-grade product is desired, for example in hydrogenating carbohydrates. Moreover, nickel in the product stream can also present a problem with waste disposal. Additive metals such as nickel can also present complications when disposing or recovering catalyst. Preferably, the catalyst contains less than 0.1 weight % nickel, more preferably, less than 0.01 weight %.

Rhenium is another metal that can present the problems discussed above for nickel. The catalyst is preferably essentially without rhenium. This means that the rhenium to ruthenium ratio in the catalyst is less than 1:20 by weight. Preferably, rhenium, if present at all, is present in less than 0.005 weight % of the catalyst. Similarly, the catalyst is preferably essentially without cobalt.

The ruthenium is disposed on a titania support. For optimum activity, the ruthenium should exist in small particles on the surface of the support. The surface of the support typically includes not only the exterior surfaces but also interior surfaces of a porous support. The support may be in a variety of forms such as powder, pellets, honeycomb, etc. The titania is composed of at least 75% rutile, more preferably at least 90% rutile, and still more preferably at least 95% rutile. For purposes of the present invention, the % rutile is measured as follows. A powdered sample of the support (or catalyst) is analyzed by x-ray diffraction using a copper x-ray source operating at 45 kV and 40 mA scanning over the range of 5 to 75 2-theta degrees. The rutile and anatase phases can be identified by comparison with the JCPDS database reference patterns. The peak height of the largest rutile peak and largest anatase peak are used for quantitation. The % rutile is determined as a percentage of its peak height divided by the sum of the heights of the largest rutile and largest anatase peaks.

Hydrogenation reactions are best controlled by using a pure titania support. The support is preferably at least 90 weight % titania, more preferably at least 99.5% titania. Because binders, such as clays, may dissolve or interfere with catalytic activity, the support preferably does not contain binders. The catalyst can also be characterized by elemental analysis; preferably the catalyst comprises 54 to 60 weight % titanium, and 36 to 40 weight % oxygen.

Although it is possible to generate a rutile support in situ by selection of processing conditions that favor the formation of rutile, better and more consistent activity and stability can be achieved by using a support with a high level of rutile (at least 75%, more preferably 90%, and still more preferably 95%) prior to depositing ruthenium on the support's surface. Titania supports having a high level of rutile phase can be purchased or prepared. A suitable support is P25 code 7709 titania, available from Degussa Corporation, Ridgefield Park, N.J. USA. This support can be used without additional calcination or thermal processing. Alternatively, titania can be prepared by known methods such as oxidation of titanium, water treatment of titanium chloride, and hydrolysis of titanium alkoxides. The support can be titania powder, but is preferably in the form of tablets, pellets, extrudates or other forms for use in a fixed bed catalyst system.

Ruthenium can be coprecipitated with titania, but for greater activity and economy it is preferably deposited onto the titania support. The ruthenium can be deposited onto a titania support by impregnating with aqueous ruthenium compositions such as aqueous ruthenium chloride. Other methods such as vapor deposition are also possible. After impregnation, water is removed by heating and the precipitated ruthenium compound reduced to the metal by reduction with hydrogen at elevated temperature. The reduction is preferably conducted at below 300° C., since reductions above this temperature have been shown to reduce the titania resulting in migration of the titanium to the ruthenium causing less of the ruthenium surface to be exposed, and loss of catalytic activity.

Catalytic systems of the invention include a ruthenium on rutile catalyst, at least one organic compound, and water. Similarly, in methods of the invention, an organic compound in the aqueous phase is reacted with hydrogen in the presence of a ruthenium on rutile catalyst. Catalysts have been described above. The at least one organic compound is in fluid (i.e., non-ice) water; this is also known as the aqueous phase.

Organic compounds that can be hydrogenated in systems of the present invention include compounds having functional groups such as C=O, C=C, N=N, —CH=N, —NH$_2$, —CN, —COOH, —NO$_2$, —C—O—C—, and —OH. Carbohydrates are a preferred class of organic compounds. In a preferred embodiment, sugars are hydrogenated to the corresponding sugar alcohols. For example, monosaccharides (such as glucose) are reduced to alditols (such as glucitol, also known as sorbitol). Sugar alcohols can be further hydrogenated to produce alcohols such as polyols and glycols. Organic acids, which can be derived by fermentation of carbohydrates, like lactic acid or succinic acid can be hydrogenated to produce alcohols, furans and lactones. In a preferred embodiment, the organic compounds are water soluble. Examples of preferred organic compounds that are hydrogenated in the present invention include: glucose, lactose, lactulose, fructose, glyceraldehyde, erythrose, arabinose, mannose, xylose, galactose, talose, sorbitol, mannitol, dulcitol, lactitol, lactulitol, xylitol, arabinitol, lactic acid, succinic acid, and itaconic acid.

An organic reactant (i.e., an organic compound or compounds prior to hydrogenation) in water is also known as a feedstock. Feedstocks can contain any of the above described organic compounds. The feedstock is preferably in liquid form. Where the feedstock contains a carbohydrate or carbohydrate derivative, the feedstock preferably comprises an organic component of about 10 to 70 weight % in aqueous solution.

In most practical applications, the catalytic system includes a batch reactor or a continuous catalyst reactor. The hydrogenation reactions may also be run on a small scale such as in the laboratory-scale reactor described in U.S. Pat. No. 5,616,154, incorporated herein by reference. In most commercial applications, the hydrogenations will be conducted in large batch or continuous reactors as are known to those skilled in the art. Continuous reactors include continuous stirred tank reactor (CSTR), fixed bed, fluidized bed, and expanded bed.

The hydrogenation reactions are conducted at temperature and pressure conditions suited for the organic reactant and desired product. The temperature is typically between about 80° C. to about 350° C., and the pressure is typically about 200 to 3000 pounds per square inch gauge (psig). More preferred ranges are 100 to 200° C. and 1000 to 2000 psig. For hydrogenation of sugars to their corresponding sugar alcohols (such as glucose to sorbitol) the temperature range is preferably between 80 and 140° C. and the hydrogen pressure is preferably between 1000 and 2000 psig.

Various embodiments of the invention can be characterized by reference to the surprisingly good properties exhibited. For example, preferred embodiments of the inventive catalyst can be characterized by their excellent stability. The stability can be measured in terms of the maintenance of catalytic activity over time while exposed to elevated temperature and pressure. In the present invention, stablity is measured as a function of the Chemical Oxygen Demand (COD) of a 5 weight % solution of phenol in water. COD is measured using the dichromate closed reflux colorimetric method, such as described in #5220D of the American Public Health Association, 1992. As it is used herein, the term "stability testing" means testing under operating conditions in a continuous flow reactor with a fixed catalyst bed, a liquid hourly space velocity (LHSV) of at least 1.4, a temperature of 350° C., and a pressure of 3000 pounds per square inch gauge (psig). In a preferred embodiment, the catalyst exhibits stability such that, after 11 weeks, sampling of the product stream shows a conversion efficiency of at least 97% (i.e., the COD of the feedstock is reduced by at least 97%). Preferably, the stability is such that, after 14 weeks, conversion efficiency is greater than 80%, more preferably greater than 90%, and still more preferably, greater than 99%. In another preferred embodiment the stability is such that, after 19 weeks, conversion efficiency is greater than 90%, more preferably greater than 95%, and still more preferably, greater than 99%.

The invention can also be characterized by its excellent catalytic activity in the conversion of sugars to their corresponding alcohols. In the examples in which sugars are hydrogenated to the corresponding sugar alcohols, conversion % and yield are measured using gas chromatography. Selectivity is defined as the percentage of the desired product out of all the products observed by gas chromatography. Thus, yield is equal to selectivity times conversion. In a preferred embodiment, the catalyst, catalytic system or method possesses catalytic activity such that, if it is tested with a glucose feedstock with a concentration of 40 weight % glucose in water, 1900 psig H$_2$, at a temperature of 100° C., and a LHSV of about 4, at least 98% of the glucose is converted and sorbitol is produced in at least a 95% selectivity, and more preferably a conversion of about 99% and a selectivity of about 97%. In other preferred embodiments, the catalyst, catalytic system or method possesses catalytic activity such that, if it is tested with a lactose feedstock with a concentration of 20 weight % lactose in water, 1900 psig H$_2$, at a temperature of 100° C., and a LHSV of at least 2, at least 99% of the lactose is converted and lactitol is produced with a selectivity of about 95 to about 98%. In another preferred embodiment, with a 20 weight % xylose solution under the same conditions and a LHSV of about 4, at least 99% of the xylose is converted and xylitol is produced with a selectivity of about 95 to about 99%.

These properties are intrinsic properties, to possess these properties does not mean that the catalyst, system or method has already experienced the conditions, but rather, if tested, will exhibit these properties. The measurement of various properties of the invention can better be understood with reference to the following examples.

EXAMPLES

Ruthenium on rutile catalyst was obtained through a custom order from Degussa Corporation. The catalyst contained 3 weight % ruthenium and 97% titania in the rutile form as measured by the x-ray diffraction technique described above. The content of ruthenium and titanium was confirmed by digesting a portion of catalyst with acid into a water solution and spraying the liquid into a plasma and analyzing the composition by atomic emission spectroscopy (ICP-AES). In the comparative example shown in Table 1, the ruthenium on anatase catalyst was also obtained through a custom order from Degussa Corporation; the anatase catalyst contained 3 weight % ruthenium and 97% titania in the anatase form as measured by the same techniques.

Aqueous phase processing tests were carried out in a fixed bed catalytic tubular reactor. For a complete description of the apparatus see Elliott et al. U.S. Pat. 5,616,154, incorporated herein by reference. The reactor consisted of 12 inches(30 cm) of 316 stainless steel tubing that was fed from a cylindrical feed tank by a reciprocating plunger pump. In addition to the reactor, there was a preheater section consisting of 7 feet (2.1 m) of ⅛ inch (3 mm) tubing. The reactor and preheater were heated by an electrical resistance furnace. Pressure was controlled in the reactor by a dome-loaded, back-pressure regulator. After passing through the pressure regulator, the product stream entered a condenser/separator system in which liquid samples were recovered. Uncondensed product gas was sampled by a gas chromatograph then passed through a flow meter and vented.

The feedstock for the initial testing was a 5% by weight phenol in water solution. All of the phenol conversion test runs were conducted at 350° C. and 3000 psig. The beginning COD of the feed solution was 120,000 mg/L. The conversion measurement is based on reduction of COD. The results of this testing are shown in Table 1. Liquid hourly space velocity (LHSV) is in units of (liters of feed)(liters of catalyst bed)$^{-1}$(hour)$^{-1}$.

TABLE 1

Catalyst stability

| Time | anatase conversion % | anatase LHSV | rutile conversion % | rutile LHSV |
|---|---|---|---|---|
| 1 week | 99.7 | 1.72 | 99.99 | 1.49 |
| 3 weeks | 99.8 | 1.66 | 99.99 | 1.66 |
| 6 weeks | 99.95 | 1.3 | 99.99 | 1.73 |
| 11 weeks | 94.7 | 1.95 | 99.99 | 1.91 |
| 14 weeks | 78 | 1.4 | | |
| 19 weeks | | | 99.99 | 1.47 |

It was surprisingly discovered that the catalyst having the rutile support had far superior stability as compared with the catalyst having the anatase support. Comparing the results from Table 1, although both catalysts initially showed excellent activity, after 11 weeks of operating at processing conditions, the activity of the catalyst having the anatase support had degraded from a 99.7% conversion efficiency to 94.7%. After 14 weeks, the activity of the anatase-supported catalyst had degraded severely (78% conversion). In comparison, the catalyst having the rutile support maintained excellent activity—better than 99% conversion after 19 weeks.

The ruthenium on rutile catalyst has surprisingly been discovered to possess superior catalytic activity in the conversion of sugars to their corresponding alcohols. Conversion % and selectivity were measured by gas chromatography and quantified by comparison to a standard solution. A comparison of the present invention (row 1) with ruthenium on other titania-containing supports described in the literature (lines rows 2–5), for the reduction of glucose to sorbitol, is presented in Table 2.

TABLE 2

Glucose Hydrogenation

| support | temp (° C.) | pressure (psig) | LHSV | feed conc. (wt %) | Ru (wt %) | feedstock conversion (%) | sorbitol selectivity (%) |
|---|---|---|---|---|---|---|---|
| rutile | 100 | 1900 | 4 | 40 | 3 | 99 | 97 |
| bentonite/titania[1] | 110 | 2300 | 1 | 50 | 1 | 99 | 96 |
| Ti/alumina[2] | 110 | 2000 | 2.5 | 50 | 3 | 49 | 98 |
| Ti/alumina[2] | 120 | 2000 | 1 | 50 | 3 | 99 | 93 |
| Ti/alumina[2] | 120 | 2000 | 2.5 | 50 | 3 | 77 | 97 |

[1]Values from Example 4 of U.S. Pat. No. 4,487,980
[2]Values from U.S. Pat. No. 4,413,152

In comparison with the glucose hydrogenation reported by Arena in U.S. Pat. No. 4,487,980, the glucose hydrogenation over the ruthenium on rutile catalyst proceeded at lower temperature and higher processing rate. Similarly, in comparison with the glucose hydrogenation over a titanium/alumina catalyst, the glucose hydrogenation over the ruthenium on rutile catalyst proceeded at lower temperature and higher processing rate. The ruthenium on rutile catalyst also produced the best combination of feedstock conversion and sorbitol yield. Thus, the present invention provides a surprisingly excellent result. Use of a ruthenium on rutile catalyst facilitates hydrogenations such that they proceed at relatively low temperature and high processing rates to produce a high yield of the desired hydrogenated product at an excellent conversion efficiency. It may be noted that conversion % is generally reduced as LHSV is increased, therefore, if the comparative examples were run at higher LHSV, the conversion % would probably be lower.

Testing with other reactants showed that the ruthenium on rutile catalyst produced outstanding results on a variety of organic compounds. For example, hydrogenations of xylose (a monosaccharide) and lactose (a disaccharide) were found to proceed at low temperature (100° C.) and high processing rate. Results from testing of these two sugars is shown in Table 3.

TABLE 3

Hydrogenations of Lactose and Xylose

| Feedstock 20 wt % | Temp (° C.) | Pressure (psig) | LHSV | feedstock conversion (%) | selectivity lactitol or xylitol |
|---|---|---|---|---|---|
| lactose | 100 | 1900 | 2 | 100 | 95 |
| lactose | 100 | 1900 | 3 | 99.7 | 96 |
| lactose | 100 | 1900 | 4 | 99.2 | 98 |
| xylose | 100 | 1900 | 4 | 100 | 99 |

Thus, the ruthenium on rutile catalyst has been demonstrated to produce excellent results with a variety of feedstocks.

CLOSURE

While some preferred embodiments of the present invention have been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:
1. A catalyst comprising an active metal on a titania support;

wherein the active metal comprises ruthenium;

wherein the titania is more than 75% rutile as measured by x-ray diffraction; and further wherein the catalyst is essentially without nickel or rhenium.

2. The catalyst of claim 1 wherein ruthenium comprises 1 to 5 weight percent of the catalyst.

3. The catalyst of claim 1 wherein ruthenium constitutes more than 98 weight percent of the active metal.

4. The catalyst of claim 1 wherein the catalyst contains less than 0.1 weight percent nickel.

5. The catalyst of claim 4 wherein the catalyst is essentially without cobalt.

6. The catalyst of claim 4 wherein the rhenium to ruthenium ratio is less than 1:100 by weight.

7. The catalyst of claim 1 wherein the titania is at least 90% rutile.

8. The catalyst of claim 7 wherein the support is at least 90 weight % titania and does not contain binders.

9. The catalyst of claim 7 wherein the catalyst comprises between 54 and 60 weight % titanium.

10. The catalyst of claim 7 wherein the titania is at least 95% rutile.

11. The catalyst of claim 7 wherein the catalyst is made by a process in which the titania contains more than 90% rutile prior to a step in which ruthenium is deposited on the support.

12. The catalyst of claim 7 having a stability such that, after 14 weeks of stability testing, the product stream shows a conversion efficiency of at least 90%.

13. The catalyst of claim 7 having a stability such that, after 19 weeks of stability testing, the product stream shows a conversion efficiency of at least 90%.

14. The catalyst of claim 7 having catalytic activity such that, if it is tested with a glucose feedstock with a concentration of 40 weight % glucose in water, 1900 psig $H_2$, at a temperature of 100° C., and a LHSV of about 4, at least 98% of the glucose is converted and sorbitol is produced with at least a 95% selectivity.

15. A catalytic system comprising a catalyst, at least one organic compound, and liquid water; and wherein the catalyst comprises an active metal on a titania support;

wherein the active metal comprises ruthenium;

wherein the titania is more than 75% rutile as measured by x-ray diffraction; and further wherein the catalyst is essentially without nickel.

16. The catalytic system of claim 15 wherein the at least one organic compound comprises a compound selected from the group consisting of carbohydrates and organic acids derived from the fermentation of carbohydrates.

17. The catalytic system of claim 15 further comprising a fixed bed continuous reactor in which the catalyst is supported.

18. The catalytic system of claim 15 wherein the at least one organic compound comprises a compound selected from the group consisting of glucose, lactose, lactulose, fructose, glyceraldehyde, erythrose, arabinose, mannose, xylose, galactose, talose, sorbitol, mannitol, dulcitol, lactitol, lactulitol, xylitol, arabinitol, lactic acid, succinic acid, and itaconic acid.

19. The catalytic system of claim 15 wherein the titania is at least 90% rutile and wherein the system possesses a stability such that, after 19 weeks of stability testing, the product stream shows a conversion efficiency of at least 95%.

20. A method of hydrogenating an organic compound in the aqueous phase comprising:

contacting a feedstock with hydrogen in the presence of a catalyst;

wherein the catalyst comprises an active metal on a titania support;

wherein the active metal comprises ruthenium;

wherein the titania is more than 75% rutile as measured by x-ray diffraction;

wherein the catalyst is essentially without nickel; and wherein the feedstock comprises at least one organic compound in water.

21. The method of claim 20 wherein the feedstock comprises a sugar, and said sugar is hydrogenated to the corresponding sugar alcohol.

22. The method of claim 20 wherein the feedstock is in liquid form.

23. The method of claim 21 wherein the titania comprises at least 90% rutile and wherein the hydrogenation is conducted at a temperature between 80 and 140° C. and a pressure between 1000 and 2000 psig.

24. The method of claim 23 wherein the method is capable of converting a feedstock of a 40 weight % glucose in water solution, at conditions of 1900 psig $H_2$, at a temperature of 100° C., and a LHSV of about 4, to achieve a glucose conversion of at least 98% and a sorbitol selectivity of at least a 95%.

* * * * *

UNITED STATES PATENT AND TRADEMARK OFFICE
CERTIFICATE OF CORRECTION

PATENT NO.  : 6,235,797 B1
DATED       : May 22, 2001
INVENTOR(S) : DC Elliot et al.

It is certified that error appears in the above-identified patent and that said Letters Patent is hereby corrected as shown below:

<u>Title page,</u>
Item [75], please change "Douglas C. Elliot" to "Douglas C. Elliott".

Signed and Sealed this

Thirtieth Day of October, 2001

*Attest:*

NICHOLAS P. GODICI
*Attesting Officer*     Acting Director of the United States Patent and Trademark Office